United States Patent [19]

Schmatz et al.

[11] Patent Number: 5,310,873
[45] Date of Patent: May 10, 1994

[54] CYCLOHEXAPEPTIDE COMPOUND

[75] Inventors: Dennis M. Schmatz, Cranford; Jan S. Tkacz, Piscataway; Robert E. Schwartz; Mervyn Turner, both of Westfield, all of N.J.

[73] Assignee: Merck & Co., Inc., Rahway, N.J.

[21] Appl. No.: 492,001

[22] Filed: Mar. 12, 1990

[51] Int. Cl.$^5$ .............. A61K 37/02; C07K 7/06; C07K 5/12
[52] U.S. Cl. .......................... 530/317; 514/9
[58] Field of Search ................ 530/317; 514/9

[56] References Cited

U.S. PATENT DOCUMENTS 4,287,120 9/1981 Abbott et al. ............... 530/317
4,931,352 6/1990 Fromtling et al. ........... 530/317

OTHER PUBLICATIONS

Schmatz, et al., "Treatment of *Pneumocystis cannii* pneumonia with 1,3,B-glucan synthesis inhibitors", 87, Proc. Natl. Acad. Sci. USA, pp. 5950–5943, 1990.

*Primary Examiner*—Merrell C. Cashion, Jr.
*Assistant Examiner*—S. G. Marshall
*Attorney, Agent, or Firm*—Richard C. Billups; Joseph F. DiPrima

[57] ABSTRACT

A cyclohexapeptide base which is the nucleus of closely related antibiotics obtained by culturing *Zalerion arboricola* and its salts are described. They are useful intermediates for the preparation of new semisynthetic compounds having antimicrobial activity.

1 Claim, No Drawings

CYCLOHEXAPEPTIDE COMPOUND

The present invention relates to a cyclohexapeptide base which may be represented by the formula

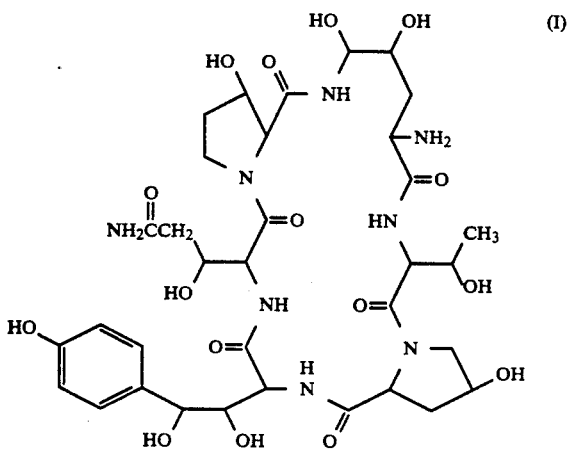

and acid additon salts thereof. The compound is a useful intermediate in the preparation of semi-synthetic compounds which have antifungal properties.

The cyclohexapeptide may be named 1-(4,5-dihydroxy-L-ornithine)-5-(3-hydroxy-L-glutamine)-6-(3-hydroxy-L-proline)echinocandin B (hereinafter Compound I). The empirical formula of Compound I is $C_{34}H_{50}N_8O_{16}$ and the molecular weight is 826.

Compound I may be retained in the form of acid addition salts. Representative acids for forming salts include hydrochloric, hydrobromic, hydroiodic, sulfuric, phosphoric, acetic, benzoic, sulfamic, tartaric, citric, maleic, succinic, ascorbic, glycolic, lactic, fumaric, palmitic, cholic, pamoic, mucic, D-glutamic, D-camphoric, glutaric, phthalic, lauric, stearic, salicylic, methanesulfonic, benzenesulfonic, sorbic, picric, cinnamic, and the like. Compound I and salts thereof are useful as intermediates in the preparation of semisynthetic compounds which have antifungal properties.

Another aspect of the present invention is a method of obtaining said cyclohexapeptide base Compound I by deacylating a compound having the formula (II).

ing application Ser. No. 374,416, filed Jun. 30, 1989, and copending applications Ser. No. 492,025 and Ser. No. 492,026 the teachings therein of production, isolation and properties are incorporated by reference.

Compound I may be prepared by subjecting Compound II in an aqueous medium, i.e., a buffer solution and solubilized with the aid of dimethyl sulfoxide, to a deacylating enzyme obtained from or present in intact cells of a microorganism of the family Actinoplanaceae or Pseudomondacea, or a microorganism made to produce the deacylating enzyme through recombinant DNA technology. The deacylation may be monitored by *Candida albicans* assay or high performance liquid chromatography (HPLC) assay and the conversion allowed to continue until deacylation is complete as indicated by the disappearance of anti-Candida activity of the substrate (Compound II) or appearance of the product (Compound I).

Compound I then may be isolated from the resulting fermentation broth by centrifuging the broth, recovering the supernatant and passing it through a column of "Diaion" HP-20 or SP-207 resin (styrene-divinylbenzene copolymer and brominated styrene-divinylbenzene copolymer respectively, Mitsubishi Chemical Industries, Ltd.) to retain Compound I on the column, then after first washing the column with deionized water, eluting with methanol to recover Compound I in the eluate. The eluate fractions are combined and concentrated to obtain crude Compound I. The latter may be further purified by cation exchange HPLC as hereafter more fully detailed.

The eluates when acylated with an activated ester of an appropriate fatty acid are converted into compounds which are active against *Candida albicans* and other fungi. Thus, the products of the present invention are useful as intermediates in the preparation of antifungal agents. The preparation and properties of these agents are the subject of copending concurrently filed application, Ser. No. 492,012.

PREPARATION OF THE STARTING MATERIAL

The starting material for the deacylation, Compound II, may be obtained by cultivating *Zalerion arboricola*, ATCC 20868, or a mutant thereof in nutrient medium until Compound II is produced, thereafter recovering

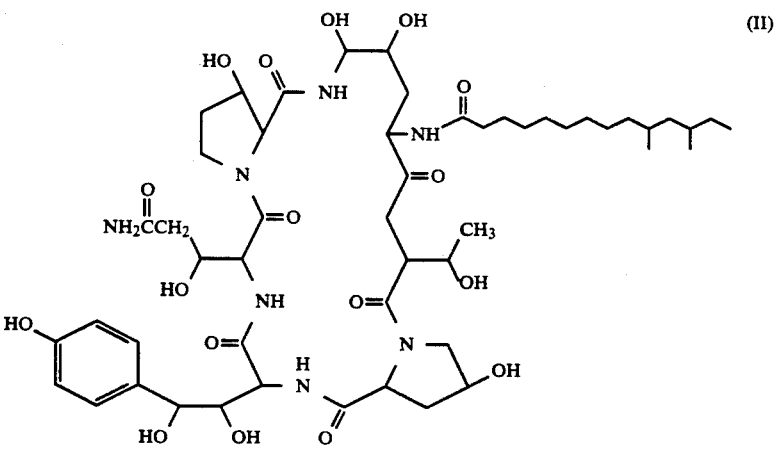

and hereinafter referred to as Compound II.

The preparation of Compound II, hereinafter described is more fully described and claimed in copend- Compound II from the nutrient medium by extracting either the mycelium or whole broth with methanol, removing the solvent from the extract to obtain a residue and thereafter dissolving the residue in a solvent suitable for chromatographic separation to recover Compound II in the eluate.

*Zalerion arboricola* ATCC 20868 is described in the aforementioned copending applications, Ser. No. 374,416 and Ser. No. 492,025 and the teachings therein are incorporated by reference. It is available from the American Type Culture Collection at 12301 Parklawn Drive, Rockville, Md. 20852. A particular mutant, *Z. arboricola* ATCC 20957, has been found to be especially useful for preferentially obtaining Compound II, the starting material. The mutant and its use in the production and isolation of Compound II is the subject of copending application Ser. No. 494,024. The teachings of these applications are incorporated by reference.

Nutrient media useful for producing Compound II are those supplying carbon, nitrogen and inorganic salts. Sources of carbon may be glycerol, sugars, sugar alcohols, starches, carbohydrate derivatives or may be complex nutrients such as oat flour, corn meal, millet and the like; sources of nitrogen may be ammonium salts or amino acids such as glycine, threonine, methionine and the like or may be complex sources such as yeast hydrolysates, yeast extracts, corn steep liquors, cottonseed meal and the like. Inorganic nutrients are supplied as customary salts, such as potassium, magnesium, calcium, phosphate, chloride, carbonate, and trace metals. Particularly important salts are ammomium and monobasic potassium phosphate salts.

In carrying out the preparation of the starting material, Compound II, the fermentation medium is inoculated with a culture growth which has been prepared from frozen vegetative mycelia or an agar slant of *Z. arboricola* in a conventional manner and the fermentation production medium incubated for from 3 to 30 days, with or without agitation at temperatures in the range of from about 20° C. to about 40° C. at a pH in the range of from about 5.0 to 8.5. At the end of the cultivation period, the active component is recovered by adding alkanol to the medium if the fermentation had been carried out in a solid medium or to the whole broth if the fermentation had been carried out in a liquid medium. The aqueous alkanol solution is filtered to remove solid impurities and then adsorbed on "Diaion" HP-20 or equivalent styrene-divinylbenzene copolymer and then eluted with 100% alkanol. This may be repeated and the crude isolate mixture subjected to chromatographic separation using conventional column chromatography with non-ionic resin such as silica gel or by high performance liquid chromatography employing reverse phase resin, or a combination thereof. With silica gel, ester/alcohol mixtures provide good separations; with dextran adsorbent, chlorohydrocarbon/hydrocarbon/alcohol system is useful. Fractions containing antibiotic Compound II may be detected by an antifungal assay using *Candida albicans* or by analytical HPLC compared to a previously determined standard. The active fractions are combined and concentrated to obtain crude Compound II. The latter may be purified, employing conventional technique such as further chromatography. It may be desirable to sterilize Compound II prior to enzymatic deacylation but is generally not required. Since Compound II is the substrate in the deacylation step, in the discussion of the step, Compound II may be referred to simply as the substrate.

The details of the production and isolation of Compound II are found described in the aforementioned copending applications, the teachings of which are incorporated by reference.

DEACYLATION

A. Deacylation Enzyme

The enzyme which is useful for deacylation is produced by certain microorganisms of the family Actinoplanaceae and Pseudomondaceae. The organisms of the Pseudomondaceae family are preferred, especially *Pseudomomas acidovorans* and *Pseudomonas diminuta*.

The Actinoplanaceae enzyme may be the same enzyme used to deacylate penicillins and described in U.S. Pat. No. 3,150,059 or that described in U.S. Pat. No. 4,299,763. Among the species and varieties of Actinoplanaceae which may be employed are *Actinoplanes philippinensis, Actinoplanes armeniacus, Actinoplanes utahensis,* and *Actinoplanes missouriensis; Spirillospora albida; Streptosporiangium roseum, Streptosporangium vulgare, Streplosporangium roseum* var. hollandensis, *Strepto sporangium album, Streptosporangium viridialbum, Amorphosporangium lariella regularis, Ampullariella campanulata, Ampullariella lobata, Ampullariella digitata; Pilimelia terevasa, Pilimelia anulata; Planomonospora parontospora, Planomonospora venezuelensis, Planobispora longispora: Planobispora rosea; Dactylosporangium aurantiacum,* and *Dactylosporangium thailendense.*

Cultures of useful species of Actinoplanaceae or Pseudomondaceae may be obtained from the American Type Culture Collection, address supra. Representative of a preferred culture for the production of the enzyme is *P. acidovorans* originally obtained as ATCC 11299B from the American Type Culture Collection and maintained as MB 3744 in the culture collection of Merck & Co., Rahway, N.J. A sample of MB 3744 has been resubmitted to the American Type Culture Collection for deposit under the Budapest Treaty and has been assigned accession no. ATCC 53942.

The morphological and cultural characteristics of the culture are as follows:

Gram-negative aerobic rod, approximately 0.8–1.0 $\mu$m × 3.0–4.0 $\mu$m. Growth occurs on trypticase soy agar at 25°–37° C. Colonies are opaque and convex with an entire margin and glistening surface. Colonies have a butyrous texture. No pigments are observed. Growth on MacConkey agar is also observed.

The biochemical characteristics of this strain are as follows: oxidase positive, gelatin is hydrolyzed, nitrate reduced to nitrite. Growth occurs by assimilation of the following carbon sources in the presence of ammonium sulfate: D-gluconate, caprate, adipate, and malate, D-mannitol, and phenylacetate.

As will be apparent to those in the field, the microorganisms which produce the enzyme are subject to variation. For example, artifical variants and mutants of these strains may be obtained by treatment with various known mutagens such as ultraviolet rays, X-rays, high-frequency waves, radioactive rays, and chemicals. All natural and artifical variants and mutants of the Pseudomondacea the Actinoplanaceae which produce the enzyme may be used in this invention.

The enzyme may be produced under conditions satisfactory for the growth of the producing organism. For the organism Actinoplanacea the conditions are generally a temperature in the range 25° to 30° C. and a pH between about 5.0 and 8.0, while employing agitation and aeration. The culture medium should contain (a) an assimilable carbon source such as sucrose, glucose, glycerol, or the like; (b) a nitrogen source such as peptone, urea, ammonium sulfate, or the like; (c) a phosphate source such as soluble phosphate salt; and (d) inorganic salts found generally to be effective in promoting the growth of microorganisms. An effective amount of the enzyme is generally obtained in from about 40 to about 60 hours after the beginning of the growth cycle and persists for some time after the effective growth has been reached.

From the organism Pseudomonas, the conditions are generally, a temperature in the range 20° to 40° C., a pH between 5.5 and 8.5 while employing agitation and aeration, The culture medium should contain (a) an assimilable carbon source such as carbohydrates, sugar alcohols and sugar derivatives, fatty acids, dicarboxylic acids, hydroxy acids, aliphatic amino acids, other amino acids and related compounds, or the like; (b) a nitrogen source such as beef extract, peptone, yeast extract, soybean digest, casein digest, brain heart infusion, or the like; (c) and inorganic salts found generally to be effective in promoting the growth of microorganisms. An effective amount of enzyme is generally obtained in from about 16 to about 48 hours after the beginning of the growth cycle.

Representative of a medium suitable for production of a deacylase by the PseudoNonas species is Luria-Bertani medium having the following composition:

|  | per liter |
|---|---|
| Bacto-Tryptone | 10 g |
| Bacto-Yeast Extract | 5 g |
| Sodium chloride | 10 g |
| No pH adjustment | |

Generally, the enzyme is envelope-bound and is not cryptic in the intact cells, thereby permitting use of resting suspensions of washed, live cells for deacylation. The amount of enzyme produced varies from species to species of the organism and in response to different growth conditions.

However, instead of using growing or resting cells, soluble or immobilized enzymes obtainable by methods known to the skilled artisan may be used. Furthermore, deacylating enzymes produced by recombinant technology with genes obtained from microorganisms also may be employed.

B. Deacylation and Recovery of Compound I

The substrate used as the starting material (Compound II) is preferably added as a solution in dimethyl sulfoxide (DMSO) to a resting suspension of washed Pseudomonas acidovorans cells in a phosphate buffer pH 6.5 after the cells have been grown in a nutrient medium for 16 to 24 hours. The concentration of substrate in the conversion medium may vary widely. For maximum use of enzyme source and for substantially complete deacylation within a 24-hour period however, the concentration of substrate will generally range from about 0.5 to about 2.0 mg/ml. Lower concentrations can be used but such may not make maximal use of the enzyme; higher concentrations may also be used but the substrate then may not completely deacylate because of its insolubility.

Alternatively, the substrate may be added to a culture of Actinoplanaceae under similar conditions.

The most suitable conditions, not only for converting the substrate antibiotic to a cyclopeptide Compound I but also for the stability of Compound I produced, are when the pH of the reaction medium is maintained in the range of from about 6.0 to about 7.0. A pH of about 6.5 is preferred.

After addition of the substrate, incubation of the culture should be continued for about 24 hours or longer. The purity of the substrate will affect the rate of deacylation. When substrates of lower purity are used, the deacylation proceeds at a slower rate. Multiple additions of substrate may be employed.

The deacylation may be carried out over a broad temperature range, i.e., from about 20° to about 60° C. Preferred temperatures are between 30° and 60° C.

The deacylation may be monitored using a *Candida albicans* assay since Compound II is very active against *C. albicans* while Compound I is biologically inactive. Both broth and alcoholic extracts of fermentation solids should be assayed since the solid is only slightly soluble in aqueous solutions.

Compound I may be separated from the fermentation broth by methods known in the art such as by centrifuging to separate the cells, loading the supernatant onto a chromatographic column, preferably SP-207 or HP-20, to adsorb Compound I thereon, and recovering from the resin by eluting with methanol and concentrating the active eluates. The eluates may be further purified by cation exchange preparative HPLC, followed by desalting on SP-207.

The following example illustrates the invention but is not to be construed as limiting.

EXAMPLE I

Compound I

A. Preparation of the Deacylating Enzyme

*P. acidovorans* ATCC 53942, maintained on slants of Luria-Bertani medium solidified with 2% agar was employed to produce the deacylation enzyme.

A seed culture was first prepared by inoculating a 50-ml portion Luria-Bertani medium with a loopful of the bacteria and the culture incubated for 24 hours at 28° C. with shaking. Cells for the deacylation were then grown by diluting the seed culture 1:500 into twenty 50 milliliter portions of fresh Luria-Bertani medium in 250 ml flasks and incubating for 16 hours at 28° C. with shaking.

Cells from one liter of culture were harvested by centrifugation at 6600 g for 20 minutes. The cells were resuspended in 1% NaCl and again collected by centrifugation at 6600 g for 20 minutes. The cells were then suspended in 475 ml of 50 mM potassium phosphate buffer, pH 6.5 and the suspension warmed to 37° C. to obtain the deacylating enzyme.

B. Preparation of Compound II (Substrate)

250 ml flasks are prepared containing 54 ml of KF seed medium of the following composition:

| KF Seed Medium | |
|---|---|
|  | per liter |
| Corn steep liquor | 5.0 g |
| Tomato paste | 40.0 g |
| Oat flour | 10.0 g |
| Glucose | 10.0 g |
| Trace elements | 10.0 ml |
| Distilled water | 1000 ml |
| pH | 6.8 |

-continued

| KF Seed Medium | |
|---|---|
| Trace elements | per liter 0.6N HCl |
| $FeSO_4.7H_2O$ | 1.0 g |
| $MnSO_4.4H_2O$ | 1.0 g |
| $CuCl_2.2H_2O$ | 0.025 g |
| $CaCl_2$ | 0.1 g |
| $H_3BO_3$ | 0.056 g |
| $(NH_4)_6MoO_{24}4H_2O$ | 0.019 g |
| $ZnSO_4.7H_2O$ | 0.2 g |

The flasks were inoculated from an agar slant of MF 5404 *Zalerion arboricola* ATCC 20957, and incubated at 25° C. for four days at 220 rpm.

A 20 ml sample of the resulting culture was used to inoculate each of four 2 liter flasks containing 500 ml of KF medium, which then were incubated at 25° C. for three days at 220 rpm. The flask contents were then pooled for use as inoculum for a 300 liter seed fermenter containing 180 liter of KF medium and 2 ml/liter of polypropylene glycol P-2000 to (Dow Chemical Co.) to reduce foaming. The seed fermenter was operated for three days at a temperature of 25° C., an air flow of 90 liter/min, a pressure of 0.7 kg/cm² gauge, and an agitator speed of 200 rpm. A 25 liter sample of the culture was used to inoculate an 800 liter production fermenter containing 475 liters of a medium (TG103) of the following composition (with 2 ml/liter polypropylene glycol P-2000):

| TG103 Production Medium | |
|---|---|
| | per liter |
| D-mannitol | 40 g |
| NZ-Amine type | 33 g |
| Fidco Yeast Extract | 10 g |
| $(NH_4)_2SO_4$ | 5 g |
| $KH_2PO_4$ | 9 g |
| Deionized water | to 1000 ml |

No initial pH adjustment; sterilized at 120° C. for 25 minutes.

The foregoing production medium is disclosed in copending application Serial No. 374,416 filed Jun. 30, 1989 and Ser. No. 492,025 and Ser. No. 492,046.

The production fermenter was operated for five days at a temperature of 25° C., an air flow of 250 liter/minute, a pressure of 0.7 kg/cm² gauge, and an agitator speed of 150 rpm. The pH was allowed to decrease from an initial value of 6.0 down to 5.5, then maintained at 5.5±0.4 using NAOH and $H_2SO_4$. After five days the broth from two batches was harvested for product isolation.

Seven hundred and fifty liters of methanol (MeOH) was added to 750 liters of fermentation whole broth and the mixture agitated for 8 hours. This whole broth extract was centrifuged to remove the insoluble fermentation solid and to yield 1436 liters of clarified supernatant the pH of which then was adjusted to 7.

A 77 liter "Diaion" SP-207 bed was prepared by washing with methanol and pre-equilibrating with 50:50 MeOH/$H_2O$ - The clarified supernatant was then charged to the "Diaion" SP-207 column in an upflow direction at a fluidized bed rate of 5.7 liters per minute. After charging, the column was washed with 567 liters of 65:35 MeOH/$H_2O$ and eluted with 454 liters 100% MEOH.

The 65:35 MeOH/$H_2O$ and 100% MEOH "Diaion" SP-207 cuts were combined and adjusted to a composition of 50:50 MeOH/$H_2O$ by the addition of $H_2O$ to yield 945 liters of product rich cuts. This product rich cut was charged to a 108 liter "Diaion" HP-20 column (washed with MEOH and pre-equilibrated with 50:50 MeOH/$H_2O$) at a flow rate of 2-4 liters per minute. The resin was then washed with 567 liters of 65:35 MeOH/$H_2O$ and eluted with 454 liters 100% MEOH.

The HP-20 cut rich in Compound IIA was concentrated to a final volume of 6 liters by first diluting with $H_2O$ and then adsorbing and eluting from a smaller HP-20 column (10 liters) in a manner similar to that employed in the larger (108 liter) HP-20 column.

Two liters (of a total of 6 liters) of the concentrated HP-20 product rich cut was diluted with 2 liters of water and charged to a preparative HPLC system equipped with a 3.9 liter Amicon C18 column prewashed with MEOH and pre-equilibrated with 50:50 MeOH/$H_2O$. The charge was followed by 500 milliliters of 50:50 MeOH/$H_2O$ and eluted at a flow rate of 212 ml/min with a linear gradient from 50:50 MeOH/$H_2O$ to 100% MEOH in a 60 minute time period. Fractions were analyzed via HPLC, combined and concentrated to dryness to yield approximately 20 grams of Compound IIA of 88 percent purity.

Deacylation and Preparation of Compound I

A 1-gram quantity of Compound II is dissolved in 25 ml of dimethyl sulfoxide and the solution added dropwise to a stirred suspension of *P. acidovorans* ATCC 53942 cells and the reaction mixture maintained at 37° C. for 18 hours whereupon deacylation is found to have been complete with the formation of Compound I as determined by *C. albicans* assay.

The reaction mixture is then centrifuged at 6600G for 20 minutes to separate the cells and to recover Compound I in the supernatant.

The supernatant is adsorbed on HP-20 resin with water. Crude Compound I is recovered from the resin by eluting with methanol and concentrating the eluates.

The eluates are combined, diluted with water, charged to a preparative HPLC system equipped with a 50 cm. Whatman Partisil 10 SCX (strong cation exchange, phenyl $SO_3$) magnum 20 column, and then eluted at 20 ml/min with 0.01M potassium phosphate (pH=6) buffer and monitored via UV at 210 nm. Cuts rich in the deacylated products were combined and the resulting mixture adsorbed and eluted from HP-20 resin with methanol to remove buffer salts and to obtain Compound I of m.w. 826.

Compound I may be acylated to provide new antibiotic substances. Thus, the compounds are useful for preparing semisynthetic derivatives useful against fungi which may have particularly desirable properties for utilization as a drug. The preparation and properties of such compounds are the subject of the concurrently filed copending application Ser. No. 490,012, previously noted.

The acylation may be accomplished by reacting Compound I with an activated derivative of the acid corresponding to the desired acyl side chain group. Briefly, Compound I is reacted with an acyl halide, an acid anhydride or an activated ester such as pentafluorophenyl, 3,4,5-trichlorophenyl, p-nitrophenyl or pentachlorophenyl ester of the acid at room temperature in an inert solvent such as dimethylformamide for 15 to 20 hours. At the end of this time, the solvent is vaporized off and the residue purified by a conventional method such as column chromatography on silica gel with ethyl acetate/methanol (3/2) as the eluting agent.

The derivatives particularly those with acyl groups greater than about 8 carbon atoms are useful to inhibit the growth of pathogenic fungi, both as an antiseptic by controlling growth on surfaces or in treating infections caused by fungi. In particular, the compounds are active against *Candida albicans* and other fungi causing mycotic infections as disclosed in the aforementioned application.

Additionally the derivative may be used for the control of filamentous fungi, especially against fungi infecting plants such as Cochliobolus Miyabeanus and Aspergilus species and against fungi infecting paper, paper products, textiles, leather, paint and other consumer goods.

We claim:

1. A cyclohexapeptide of the formula

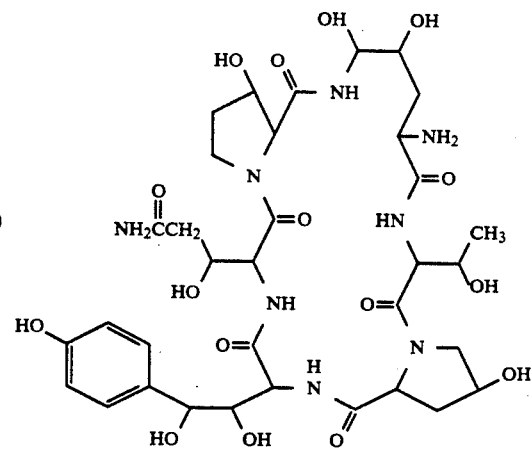

and acid addition salts thereof.